United States Patent [19]

Weiss

[11] Patent Number: 6,090,557

[45] Date of Patent: Jul. 18, 2000

[54] *NEISSERIA GONORRHOEAE*-SPECIFIC OLIGONUCLEOTIDES

[75] Inventor: Judith Barbara Weiss, Alameda County, Calif.

[73] Assignee: Roche Molecular Systems, Inc., Pleasanton, Calif.

[21] Appl. No.: 09/057,929

[22] Filed: Apr. 9, 1998

Related U.S. Application Data

[60] Provisional application No. 60/070,914, Apr. 18, 1997.

[51] Int. Cl.[7] .............................. C12Q 1/68; C12P 19/34; C07H 21/02; C07H 21/04

[52] U.S. Cl. ................................ 435/6; 435/5; 435/91.1; 435/91.2; 435/810; 536/23.1; 536/24.3; 536/24.31; 536/24.32; 536/24.33

[58] Field of Search .................................. 435/5, 6, 91.1, 435/91.2, 810; 536/23.1, 243, 24.31, 24.32, 24.33

[56] References Cited

U.S. PATENT DOCUMENTS

| | | | |
|---|---|---|---|
| 5,256,536 | 10/1993 | Miyada et al. | 435/6 |
| 5,525,717 | 6/1996 | Miyada et al. | 536/24.32 |
| 5,550,040 | 8/1996 | Purohit et al. | 435/91.2 |

OTHER PUBLICATIONS

Miyada et al, "A DNA sequence for the discrimination of Neisseria gonorrheae from other Neisseria species", Mol. Cell. Probes 5:327–335, 1991.

1996, Roche Diagnostics Systems, Inc. Amplicor® product insert for "Chlamydia trachomatis/Neisseria gonorrhoeae (CT/NG) test."

*Primary Examiner*—Jeffrey Fredman
*Attorney, Agent, or Firm*—Douglas A. Petry

[57] ABSTRACT

The present invention relates to oligonucleotides which hybridize specifically to the cytosine DNA methyltransferase gene of *Neisseria gonorrhoeae* and distinguish the cytosine DNA methyltransferase gene of *N. gonorrhoeae* from highly homologous sequences which have been discovered in some strains of other species of the genus Neisseria. The oligonucleotides are useful as primers for the polymerase chain reaction (PCR) amplification of a nucleic acid sequence from the cytosine DNA methyltransferase gene of *N. gonorrhoeae* and in *N. gonorrhoeae* amplification/detection assays.

18 Claims, No Drawings

NEISSERIA GONORRHOEAE-SPECIFIC OLIGONUCLEOTIDES

This application claims benefit of Provisional Application Serial No. 60/070,914 filed Apr. 18, 1997.

BACKGROUND OF THE INVENTION

1. Field of the Invention

The present invention relates to the field of molecular biology and nucleic acid chemistry. More specifically, it relates to methods and reagents for amplifying *Neisseria gonorrhoeae* nucleic acid. The invention therefore has applications in the detection of *Neisseria gonorrhoeae*, the field of medical diagnostics generally, and the field of molecular biology.

2. Description of Related Art

*Neisseria gonorrhoeae* is the causitive agent of gonorrhea, one of the most commonly reported bacterial infections in the United States.

Miyada and Born, 1991, *Mol. Cell. Probes* 5:327–335; U.S. Pat. No. 5,256,5365; and U.S. Pat. No. 5,525,717; each incorporated herein by reference, describe the detection of *N. gonorrhoeae* using a DNA probe derived from a genomic fragment containing an open reading frame (ORF 1) having significant homology with the sequence of the *N. gonorrhoeae* cytosine DNA methyltransferase gene (M.Ngo PII). Probes derived from this sequence were shown to hybridize to purified DNA from 105/106 *N. gonorrhoeae* strains tested in a dot blot format. Cross-reactivity with other Neisseria species was observed only with *N. mucosa*, however this cross-reactivity was eliminated using a high stringency wash.

The invention of the methods for amplifying specific sequences of nucleic acids, in particular, the polymerase chain reaction (PCR), makes possible the rapid detection of nucleic acids present in a sample in what was previously an undetectably low quantity (see U.S. Pat. Nos. 4,683,195; 4,683,202; and 4,965,188, each of which is incorporated herein by reference). The development and application of PCR are described extensively in the literature. For example, a range of PCR-related topics are discussed in PCR Technology—principles and applications for DNA amplification, 1989, (ed. H. A. Erlich) Stockton Press, New York; PCR Protocols: A guide to methods and applications, 1990, (ed. M. A. Innis et al.) Academic Press, San Diego; and PCR Strategies, 1995, (ed. M. A. Innis et al.) Academic Press, San Diego; each of which is incorporated herein by reference. Commercial vendors, such as Perkin Elmer (Norwalk, Conn.), market PCR reagents and publish PCR protocols.

Since the original description of nucleic acid amplification, various primer-based nucleic acid amplification methods have been described including, but are not limited to, Ligase Chain Reaction (LCR, Wu and Wallace, 1989, *Genomics* 4:560–569 and Barany, 1991, *Proc. Natl. Acad. Sci. USA* 88:189–193); Polymerase Ligase Chain Reaction (Barany, 1991, *PCR Methods and Appl.* 1:5–16); Gap-LCR (PCT Patent Publication No. WO 90/01069); Repair Chain Reaction (European Patent Publication No. 439,182 A2), 3SR (Kwoh et al., 1989, *Proc. Natl. Acad. Sci. USA* 86:1173–1177; Guatelli et al., 1990, *Proc. Natl. Acad. Sci. USA* 87:1874–1878; PCT Patent Publication No. WO 92/0880A), and NASBA (U.S. Pat. No. 5,130,238). All of the above references are incorporated herein by reference. A survey of amplification systems is provided in Abramson and Myers, 1993, *Current Opinion in Biotechnology* 4:41–47, incorporated herein by reference.

Purohit and Silver, U.S. Pat. No. 5,550,040, incorporated herein by reference, describe the detection of *N. gonorrhoeae* using a PCR amplification/detection assay. Based on a comparison of DNA sequences from various different strains of *N. gonorrhoeae* described in the literature, primers were designed to amplify a 201 nucleotide target sequence within the sequence provided by Miyada and Born, supra. The primers amplified the target sequence from all strains of *N. gonorrhoeae* tested, although DNA from some strains of *N. mucosa* was also amplified. The amplified product was then hybridized with an *N. gonorrhoeae*-specific probe to achieve the desired specificity. The resulting amplification/detection assay was observed to detect all strains of *N. gonorrhoeae* tested without cross-reactivity with non-*N. gonorrhoeae* DNA.

Patients infected with *N. gonorrhoeae* often also are infected with *Chlamydia trachomatis*. The *N. gonorrhoeae* primers described in the '040 patent were used in conjunction with primers for the amplification of *C. trachomatis* to amplify target sequences from either organisms in a single amplification reaction. The co-amplification reaction, followed by separate species-specific hybridization reactions, formed the basis of an amplification/detection assay able to detect and distinguish infection with *N. gonorrhoeae*, *C. trachomatis*, or both.

The AMPLICOR® *Chlamydia trachomatis/Neisseria gonorrhoeae* (CT/NG) Test, commercially available from Roche Diagnostic Systems, Inc. (Branchburg, N.J.), is an in vitro assay for the qualitative detection of *Chlamydia trachomatis* and/or *Neisseria gonorrhoeae* in clinical samples which is based on the assay described in the '040 patent. The AMPLICOR® *Chlamydia trachomatis/Neisseria gonorrhoeae* (CT/NG) Test product insert is incorporated herein by reference.

Conventional techniques of molecular biology and nucleic acid chemistry, which are within the skill of the art, are explained fully in the literature. See, for example, Sambrook et al., 1989, *Molecular Cloning—A Laboratory Manual*, Cold Spring Harbor Laboratory, Cold Spring Harbor, N.Y.; *Oligonucleotide Synthesis* (M. J. Gait, ed., 1984); *Nucleic Acid Hybridization* (B. D. Harnes and S. J. Higgins. eds., 1984); and a series, *Methods in Enzymology* (Academic Press, Inc.), all of which are incorporated herein by reference. All patents, patent applications, and publications cited herein, both supra and infra, are incorporated herein by reference.

SUMMARY OF THE INVENTION

I have discovered that commercially available detection assays based on the putative cytosine DNA methyltransferase gene sequence disclosed by Miyada and Born, supra, (designated herein, "Ng-CDMT") give an unexpectedly high rate of false positive results from certain clinical samples, in particular, from throat swab samples. Further, I have determined that the cause of the false positive results is, unexpectedly, the presence of at least a portion of the *N. gonorrhoeae*-specific Ng-CDMT gene target sequence in some isolates of species of Neisseria other than *N. gonorrhoeae*.

I have discovered, identified, and characterized a number of Neisseria isolates in human throat specimens and some genital specimens which caused the false positive results. Biochemical analysis of the isolates identified them as Neisseria species other than *N. gonorrhoeae*, primarily *N. subflava* or *N. cinerea*. It was previously believed that Neisseria species other than *N. gonorrhoeae*, including *N.*

*subflava* and *N. cinerea*, do not contain the Ng-CDMT gene sequence, and I have confirmed that the majority of isolates do not contain the Ng-CDMT gene sequence. The presence of the Ng-CDMT gene sequence in a minority of isolates of Neisseria species other than *N. gonorrhoeae* represents a problem for detection assays based on the Ng-CDMT gene sequence which previously was not recognized. The present invention provides a solution to this problem.

I have determined the nucleotide sequence of a portion of the Ng-CDMT gene from a number of the newly discovered isolates of Neisseria species other than *N. gonorrhoeae* which contain the Ng-CDMT gene sequence. The gene sequences contained in these newly discovered isolates contain minor differences relative to the corresponding *N. gonorrhoeae* Ng-CDMT gene sequence. The nucleotide sequence differences which distinguish the Ng-CDMT gene sequence in the newly discovered isolates from the *N. gonorrhoeae* Ng-CDMT gene sequence are confined to a small number of positions and are conserved among the isolates. The discovery of these nucleotide sequence differences, and the localized nature of the differences, is an important aspect of the present invention.

One aspect of the present invention relates to oligonucleotides which distinguish by selective hybridization under suitably stringent conditions the Ng-CDMT gene sequence from *N. gonorrhoeae* from the corresponding Ng-CDMT sequence found in the newly discovered isolates. The oligonucleotides can be used as hybridization probes or, preferably, as amplification primers. Use of the oligonucleotides enables a significant reduction of false positives results in *N. gonorrhoeae* amplification/detection assays which target the Ng-CDMT gene sequence.

Another aspect of the invention relates to methods for amplifying a region of the *N. gonorrhoeae* Ng-CDMT gene, which methods comprise carrying out a amplification reaction using a primers (or oligonucleotides to be ligated) including an oligonucleotide of the present invention.

Another aspect of the invention relates to kits which contain an oligonucleotide of the present invention, preferably for use as an amplification primer. These kits can include additional reagents, such as the detection probes or one or more amplification reagents, e.g., polymerase, buffers, and nucleoside triphosphates.

DETAILED DESCRIPTION OF THE INVENTION

To aid in understanding the invention, several terms are defined below.

The terms "nucleic acid" and "oligonucleotide" refer to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, as well as double- and single-stranded RNA.

Oligonucleotides can be prepared by any suitable method, including, for example, cloning and restriction of appropriate sequences and direct chemical synthesis by a method such as the phosphotriester method of Narang et al., 1979, *Meth. Enzymol.* 68:90–99; the phosphodiester method of Brown et al, 1979, *Meth. Enzymol.* 68:109–151; the diethylphosphoramidite method of Beaucage et al., 1981, *Tetrahedron Lett.* 22:1859–1862; and the solid support method of U.S. Pat. No. 4,458,066, each incorporated herein by reference. A review of synthesis methods is provided in Goodchild, 1990, *Bioconjugate Chemistry* 1(3): 165–187, incorporated herein by reference.

The term "hybridization" refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which only fully complementary nucleic acid strands will hybridize are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair concentration of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, N.Y.; and Wetmur, 1991, Critical Review in Biochem. and Mol. Biol. 26(3/4) :227–259; both incorporated herein by reference).

The term "probe" refers to an oligonucleotide capable of selectively hybridizing to a target nucleic acid under suitable conditions. The probe will contain a "hybridizing region" exactly or substantially complementary to the target sequence, and will be exactly complementary to the target sequence at a variable site. A hybridization assay carried out using the probe under sufficiently stringent hybridization conditions enables the selective detection of a specific target sequence. For use in a hybridization assay for the discrimination of single nucleotide differences in sequence, the probe hybridizing region is preferably from about 15 to about 35 nucleotides in length. One of skill in the art will recognize that, in general, the exact complement of a given probe is similarly useful as a probe.

The term "primer" refers to an oligonucleotide capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. The primer will contain a "hybridizing region" exactly or substantially complementary to the target sequence, and will be exactly complementary to the target sequence at a variable site. An amplification in which primer extension is carried out under sufficiently stringent hybridization conditions allows the selective amplification of a specific target sequence. For use in a sequence-specific amplification reaction for the discrimination of single nucleotide changes in sequence, the primer hybridizing region is preferably from about 15 to about 35 nucleotides in length. Because primer extension occurs at the 3' end of the oligonucleotide, the variable site preferably is situated at the 3' end of the primer to facilitate sequence discrimination.

Probes and primers can either consist entirely of the hybridizing region oligonucleotide or can contain additional features which allow for the detection or immobilization of the oligonucleotide, but which do not significantly alter the hybridization characteristics of the hybridizing region. For example, the probe hybridizing region may be bound to a poly-T "tail", which is used to immobilize the probe to a solid support for use in the reverse dot-blot assay. Similarly, primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning of the amplified product.

As used herein, the "upstream" primer refers to the primer whose extension product is a subsequence of the coding strand. The "downstream" primer refers to the primer whose extension product is a subsequence of the complementary non-coding strand.

The terms "target sequence", "target region", and "target nucleic acid" refer to a region of a nucleic acid which is to be amplified, detected, or otherwise analyzed.

The term "variable site" or "variable position" herein refers to those nucleotide positions within the Ng-CDMT gene at which the nucleotide present differs in sequences obtained from different source organisms.

As used herein, an oligonucleotide is "specific" for a target sequence if the number of mismatches present between the oligonucleotide and the target sequence is less than the number of mismatches present between the oligonucleotide and non-target sequences which might be present in a sample. Hybridization conditions can be chosen under which stable duplexes are formed only if the number of mismatches present is no more than the number of mismatches present between the oligonucleotide and the target sequence. Under such conditions, the target-specific oligonucleotide can form a stable duplex only with a target sequence. Thus, the use of target-specific primers under suitably stringent amplification conditions enables the specific amplification of those sequences which contain the target primer binding sites. Similarly, the use of target-specific probes under suitably stringent hybridization conditions enables the detection of a specific target sequence.

The term "amplification reaction mixture" refers to a solution containing reagents necessary to carry out an amplification reaction, and typically contains primers, a thermostable DNA polymerase, dNTP's, and a divalent metal cation in a suitable buffer. A reaction mixture is referred to as complete if it contains all reagents necessary to carry out the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and, that reaction components are combined prior to the reaction to create a complete reaction mixture. Furthermore, it will be understood by one of skill in the art that reaction components are packaged separately for commercialization and that useful commercial kits may contain any subset of the reaction components which includes the modified primers of the invention.

The term "the complement of" or "the exact complement of" a given nucleic acid refers specifically to the nucleic acid which is both the same length as, and exactly complementary to, the given nucleic acid. Thus, the complement of a nucleic acid refers to a single, uniquely defined sequence.

The gene sequence of the putative *N. gonorrhoeae* cytosine DNA methyltransferase (Ng-CDMT) gene is shown in Table 1, below. The sequence corresponds to the ORF1 sequence provided by Miyada and Born, supra, but with corrections in the sequence. A sequencing error in the Miyada and Born sequence resulted in an incorrect identification of a stop codon upstream of the actual stop codon and, consequently, a truncated version of the actual open reading frame was reported. The sequence below includes the first 1067 bases of the open reading frame.

Although only one strand (the coding sequence) of nucleic acid is shown in Table 1, those of skill in the art will recognize that SEQ ID NO: 1 identifies a region of double-stranded genomic nucleic acid, and that the sequences of both strands are fully specified by the sequence information provided.

TABLE 1

| SEQ ID NO: 1 | | | | | |
|---|---|---|---|---|---|
| ATGCTATCTA AACAAATCTC AAATCTTAAT TCTTCTAGTA ACAAACCAAA AATCCTATCT | | | | | 60 |
| CTATTTTCAG GATGTGGCGG TTTGTATTTG GGCTTTCATC AAGCTGGTTG TGAAACTGTT | | | | | 120 |
| TGGGCGAACG ATTTCTCCCA TTGGGCTTGC GAAAGTTTCC GTAAAAATAT CGGCGATGTC | | | | | 180 |
| ATCGTAGAAG GTGATATTGA ACAAATTAAT CCGAATGATC CAACTATTCC CGATTGCGAC | | | | | 240 |
| ATCATTTTAG GCGGATTCCC TTGTCAAGAT TTTTCCATGA TTTGGAAACA GCCGGGCTTA | | | | | 300 |
| GAGGGTGAGC GCGGCAATCT TTATAAAAGC TTTTTACGTT TTGTAAATGC AAAAAAACCG | | | | | 360 |
| AAAGTTTTTG TTGCTGAGAA TGTGAAAGGT TTATTGACTG CCAACAAGAA AAAGCCATC | | | | | 420 |
| CAGCAAATTA TTACCGACTT TGAAAATTGC GGTTATTACG TTCAGGCGAA GCTGTATAAC | | | | | 480 |
| TTTGCAGAAT TTGGCGTACC TCAATTTCGT GAACGTGTGC TGATTGTCGG AGTACGTTTG | | | | | 540 |
| GATACAGGAT TTGATTTTCG CCATCCGGAA CCGACGCACA ATGAAACTGG CGAAAACGGC | | | | | 600 |
| TTAAAACCAT ATGTAACAGC AGGTCAGGCC ATATCCAATA TTCCACAAAA TGCCAGTAAT | | | | | 660 |
| AATGAATTAC TGAAAATCAG CGGTAAAACA CGCCGTATGT TCGAATTAAT TCCTGAAGGT | | | | | 720 |
| GGAAATTTTA CCGATATTCC TAAAGATCAT CCTTTATATG TGAAAGGTAT GATTAGCCAC | | | | | 780 |

TABLE 1-continued

SEQ ID NO: 1

```
GTTTATCGTC GTATGCATCG GAACGAGCCA TCAAAAACAA TTATTGCAGC AGGTGGCGGT  840

GGTACTTGGG GCTATCACTT CCCTGAACCG CGTGCTTTTA CTAATAGAGA ACGAGCAAGG  900

CTTCAAAGTT TTCCTGATGA TTTTGAGTTT GTCGGATCAA CAACTGAAGT ACGTCGCCAG  960

ATTGGTAATG CTGTTCCTCC TCAGGGCGTG GTTGAACTGG CAAAAAGCAT TTTACCGATT 1020

TTTTCAGACA ACTATGAGAA AGTAGATTTG CATGAGAAAT TAGTCGA              1067
```

The variable sites within SEQ ID NO: 1 which can be used to distinguish the N. gonorrhoeae Ng-CDMT gene sequence are at nucleotide position numbers 618, 621, 627, 630, 636, 653, 654, 669, 678, 681, 683, 702. These variable positions are shown highlighted and underlined in Table 1.

The particular variant nucleotides found at the variable sites within the corresponding Ng-CDMT sequence of several of the newly discovered non-N. gonorrhoeae strains are shown in table 2, below. The sequence variants shown are representative of most of the newly discovered strains. A "–" indicates that the nucleotide is the same as in SEQ ID NO: 1. The sequences shown illustrate the conserved nature of the sequence within the non-N. gonorrhoeae strains.

TABLE 2

| Strain | Nucleotide Position | | | | | | | | | | | |
|---|---|---|---|---|---|---|---|---|---|---|---|---|
| | 618 | 621 | 627 | 630 | 636 | 653 | 654 | 669 | 678 | 681 | 683 | 702 |
| 12-2 | T | T | – | G | T | T | T | – | T | T | A | G |
| 16-3 | T | T | A | A | T | T | T | G | T | T | A | G |
| Pitts | T | T | A | G | T | T | T | G | T | T | A | A |

In addition to the representative sequence variations shown above, a single isolate of N. s. flava was discovered which contained a sequence that, among the above variable positions, differed from SEQ ID NO: 1 only at positions 683 and 702 ("A" and "G", respectively). Because of the low frequency of this isolate, oligonucleotides which discriminate based on the other variable positions will still significantly reduce the occurrence of false positive results.

N. gonorrhoeae-Specific Oligonucleotides

One aspect of the invention relates to oligonucleotides which are specific to N. gonorrhoeae and distinguish the N. gonorrhoeae Ng-CMDT gene sequence from the corresponding sequence found in the newly discovered isolates. The N. gonorrhoeae-specific oligonucleotides of the present invention are oligonucleotides that are exactly complementary to either strand of SEQ ID NO: 1 (the target sequence) in a region which encompasses at least one, preferably more, of the variable positions identified above. Because of the proximity of the variable positions, typically an oligonucleotide can be chosen to encompass multiple variable sites. For example, the amplification primer described below, JW80 (SEQ ID NO: 3), encompasses positions 618, 621, 627, 630, and 636. Depending on the number of variable positions encompassed with the hybridization region and the intended use, the N. gonorrhoeae-specific oligonucleotides of the present invention preferably are from about 15 to about 50 nucleotides in length, more preferably from about 15 to about 35 nucleotides in length.

The N. gonorrhoeae-specific oligonucleotides of the present invention are useful in reactions which rely on the selective hybridization of oligonucleotides to detect or identify N. gonorrhoeae nucleic acid. Selective hybridization is based on the difference in the stability of hybridization duplexes with target and non-target nucleic acid sequences, which differ in the degree of complementarity. Under sufficiently stringent hybridization conditions, only duplexes formed between the oligonucleotide and target sequences will be stable. The presence of stable hybridization duplexes can be detected by any of a number of well known methods, such as by the use of labeled oligonucleotides, i.e., probes, or by the ability to carry out a primer extension reaction or ligation reaction, as in an amplification reaction.

In an alternative embodiment, the N. gonorrhoeae-specific oligonucleotides of the present invention are substantially complementary, i.e., containing no more than about three mismatches, to either strand of SEQ ID NO: 1 (the target sequence) in a region which encompasses at least one, preferably more, of the variable positions, and which is exactly complementary to the target sequence at one or more of the variable positions encompassed. Because mismatches which occur at non-variable positions are mismatches with both the N. gonorrhoeae target sequence and the closely related non-N. gonorrhoeae, non-target sequence, the difference in the number of mismatches in a duplex formed with the target sequence and in a duplex formed with the corresponding non-target sequence is the same as when an oligonucleotide exactly complementary to the target sequence is used. In this embodiment, the hybridization conditions are relaxed sufficiently to allow the formation of stable duplexes with the target sequence, while maintaining sufficient stringency to preclude the formation of stable duplexes with non-target sequences. Under such sufficiently stringent hybridization conditions, an oligonucleotide substantially complementary to the N. gonorrhoeae target sequence in a region which encompasses one or more variable positions, and which is exactly complementary to the target sequence at any variable positions, will hybridize only to the target sequence. Thus, oligonucleotides which are substantially complementary to either strand of SEQ ID NO: 1 (the target sequence) in a region which encompasses at least one of the variable positions, and which are exactly complementary to the target sequence at one or more of the variable positions encompassed, are within the scope of the invention.

The use of substantially, rather than exactly, complementary oligonucleotides may be desirable in assay formats in which optimization of hybridization conditions is limited. Because mismatches decrease the stability of the probe/target hybridization duplex, and thus alter the hybridization conditions needed to provide sufficient stringency for the assay, the incorporation of mismatches into the design of a probe can be used to adjust duplex stability when the assay format precludes adjusting the hybridization conditions. The effect of a particular introduced mismatch on duplex stability is well known, and the resulting duplex stability routinely can be both estimated and empirically determined, as described above.

N gonorrhoeae-Specific Oligonucleotides as Amplification Primers

In one embodiment of the present invention, sequence-specific amplification is carried out using as a primer an N. gonorrhoeae-specific oligonucleotide of the present invention. Amplification conditions are chosen such that amplification occurs only if the target sequence is present in the sample. In this manner, the N. gonorrhoeae Ng-CDMT sequence is identified by the presence or absence of amplification product. The detection of amplified product can be carried out by any of the methods well known in the art, such as analysis by gel electrophoresis. Although no additional sequence analysis of the amplified product is required, detection preferably is carried out by probe hybridization with an N. gonorrhoeae-specific probe to provide an additional level of specificity.

The hybridization specificity of the primers is a critical property of the primers which enables sequence-specific amplification. In general, the 3' end, which is the primer extension site, is more critical to the specificity of the primer because a mismatch at the 3' end can destabilize the 3' end and interfere with primer extension even though the 5' portion of the primer is hybridized to the target sequence. Thus, for the discrimination of single nucleotide changes in sequence, and to maximize the abililty to discriminate multiple nucleotide changes in sequence, it is preferable that the primer sequence hybridize to the target sequence such that the 3' end of the primer hybridizes at or near a variable position. Stated equivalently, the region of the target sequence to which the primer hybridizes preferably should contain a variable position at or near the 5' end of the region (the 3' end of the primer binds to the 5' end of the region of the target sequence). Sequence-specific amplification and the effects of primer mismatches are described in Ugozzoli et al., 1991, Methods: A Companion to Methods in Enzymology 2:42–48; Kwok et al., 1990, *Nucleic Acids Research* 18:999–1005; and Kwok et al., 1994, *PCR Methods and Applications* 3S:39–47, each incorporated herein by reference.

An additional sequence containing a restriction enzyme cleavage site (restriction sites) can be added to the 5' end of a primer without affecting the ability of the primer to be extended. The restriction site, which is incorporated into the amplified product, facilitates cloning the amplified product for use in, for example, sequencing (see U.S. Pat. No. 4,683,195). Typically, sequences between about 2 and about 10 bases in length which are not complementary to the target sequence can be added to the 5' end of the primer hybridizing region without significantly altering the ability of the primers to catalyze the specific amplification of the N. gonorrhoeae Ng-CDMT sequence. The exact length and sequence of the added 5' terminal sequences will be determined by the restriction site desired. One of skill in the art will realize that minor optimization of the amplification conditions may be necessary depending on the sequence added. However, one of skill in the art will also recognize that, for use in the present methods, a primer lengthened with an additional sequence at the 5' end which contains a restriction enzyme cleavage site is essentially equivalent to the unlengthened primer.

In a preferred embodiment, the N. gonorrhoeae-specific oligonucleotides of the present invention are used as primers in the polymerase chain reaction (PCR). However, the invention is not restricted to any particular amplification system. In general, specificity of primer-based amplification reactions depends on the specificity of primer hybridization. Thus, the N. gonorrhoeae-specific oligonucleotides of the present invention may improve the specificity of any of the primer-based amplification reactions, including those amplification methods described in the references cited in the background section, above. As other systems are developed, those systems may benefit from the enhanced specificity of the present oligonucleotides.

Particular oligonucleotides for use preferably as PCR amplification primers are shown below. The primers represent a significant improvement over primers previously described in that they discriminate between the N. gonorrhoeae Ng-CDMT sequence and the Ng-CDMT sequences found in those isolates of non-N. gonorrhoeae species of Neisseria which contain a Ng-CDMT sequence. The oligonucleotides shown below are suitable for use as upstream primers in a PCR. It will be clear to one of skill in the art that the exact complements of these oligonucleotides are useful as downstream primers in a PCR and, furthermore, that these oligonucleotides, or the exact complements thereof, could also be used as hybridization probes to identify the N. gonorrhoeae Ng-CDMT sequence. The nucleotide sequences of the primers are provided below, shown left to right in a 5' to 3' orientation.

*N. gonorrhoeae*-specific Oligonucleotide Primers

```
JW79 (SEQ ID NO: 2)   CATATGTAACAGCAGGTCAGGCC
JW80 (SEQ ID NO: 3)   TAACAGCAGGTCAGGCCATATCC
JW87 (SEQ ID NO: 4)   CGGTAAAACACGCCGTATGTTC
```

The particular oligonucleotides shown above, when used as upstream primers in a PCR, are paired with suitable downstream primers. The particular downstream primer used is not a critical aspect of the invention. Suitable downstream primers can be selected from those described in the cited references or can be designed from SEQ ID NO: 1 following the guidance provided herein. Particular preferred downstream primers for use with the above upstream primers are shown below. Primer SS02 (SEQ ID NO: 5) is described in U.S. Pat. No. 5,550,040, incorporated herein by reference. One of skill in the art will recognize that any of the oligonucleotides described in the '040 patent, such as a probe sequence or the complement of an upstream primer sequence, can be used as a downstream primer. The JW downstream primer sequences shown below were designed to provide improved amplification specificity and sensitivity. The nucleotide sequences of the downstream primers are provided below, shown left to right in a 5' to 3' orientation.

*N. gonorrhoeae*-specific Downstream Primers

```
SS02 (SEQ ID NO: 5)   AACAGCATTACCAATCTGGCGAC
JW88 (SEQ ID NO: 6)   GACGTACTTCAGTTGTTGATCCG
JW89 (SEQ ID NO: 7)   CGACGTACTTCAGTTGTTGATCCG
JW90 (SEQ ID NO: 8)   CAGTTGTTGATCCGACAAACTCA
```

Amplifications are carried out under conditions which enable amplification of the N. gonorrhoeae Ng-CDMT gene sequence, but which are sufficiently stringent to avoid amplification of non-target sequences. Preferred amplification reaction conditions are described in the examples, in U.S. Pat. No. 5,550,040, and in the product insert of the AMPLICOR® Chlamydia trachomatis/Neisseria gonorrhoeae (CT/NG) Test. The exact conditions are not a critical aspect of the invention. Optimization of amplification conditions can be carried out routinely based on the guidance provided herein.

The primers of the present invention may be used to amplify either DNA or RNA. The amplification of RNA using a reverse transcription/polymerase chain reaction (RT-PCR) is well known in the art and described in U.S. Pat. Nos. 5,322,770 and 5,310,652; Myers and Gelfand, 1991, *Biochemistry* 30(31):7661–7666; and Young et al., 1993, *J. Clin. Microbiol.* 31(4):882–886, each incorporated herein by reference.

Sample preparation methods suitable for amplification of *N. gonorrhoeae* nucleic acid are described in the examples, in U.S. Pat. No. 5,550,040, and in the product insert of the AMPLICOR® *Chlamydia trachomatis/Neisseria gonorrhoeae* (CT/NG) Test. The particular method used is not a critical aspect of the present invention. One of skill in the art can select and optimize suitable sample preparation methods based on the guidance provided herein. A suitable sample preparation kit for the amplification of *N. gonorrhoeae* DNA is commercially available as part of the AMPLICOR® *Chlamydia trachomatis/Neisseria gonorrhoeae* (CT/NG) Test.

The amplification primers and methods of the present invention are suitable for any application which uses amplified nucleic acid. For example, cloning and/or sequencing of *N. gonorrhoeae* sequences is facilitated by the use of the present primers. Methods for detecting PCR amplified nucleic acids are well known in the art. The method used to analyze the amplified nucleic acid is not a critical aspect of the invention, and any suitable method may be used.

*N. gonorrhoeae*-Specific Oligonucleotides as Probes

Each of the variable positions described above represents a single base pair difference between the *N. gonorrhoeae* target sequence and the closely related sequences found in non-*N. gonorrhoeae* species. Single base pair differences in sequence can be detected by differential hybridization of oligonucleotide probes. The probe hybridizing sequence and sequence-specific hybridization conditions are selected such that a single mismatch at the polymorphic site destabilizes the hybridization duplex sufficiently so that it is effectively not formed. The hybridization conditions depend on the exact size and sequence of the probe, and can be selected empirically using the guidance provided herein and in the prior art. The use of oligonucleotide probes to detect single base pair differences in sequence is described in Conner et al., 1983, *Proc. Natl. Acad. Sci. USA* 80:278–282, which is incorporated herein by reference.

The proportional difference in stability between a perfectly matched and a single-base mismatched hybridization duplex depends on, among other things, the length of the hybridized oligonucleotides. Duplexes formed with shorter probe sequences are destabilized proportionally more by the presence of a mismatch. In practice, oligonucleotides between about 15 and about 35 nucleotides in length are preferred for sequence-specific detection. Furthermore, because the ends of a hybridized oligonucleotide undergo continuous random dissociation and re-annealing due to thermal energy, a mismatch at either end destabilizes the hybridization duplex less than a mismatch occurring internally. Preferably, for discrimination of a single base pair change in target sequence, the probe sequence is selected which hybridizes to the target sequence such that the polymorphic site occurs in the interior region of the probe.

The difference in stability between a perfectly matched and a mismatched hybridization duplex also depends on the number of mismatches in the mismatched hybridization duplex. Because of the proximity of the variable positions, probes which encompass multiple positions easily are designed and, because of the greater difference in stability, are preferrable. The greater difference in stability also allows the use of longer hybridization probes, which increases the target specificity, while maintaining the ability to discriminate against the closest non-target sequence. Probes which encompass multiple variable positions can be up to at least about 50 nucleotides in length.

The above criteria for selecting a probe sequence which hybridizes to SEQ ID NO: 1 apply to the hybridizing region of the probe, i.e., that part of the probe which is involved in hybridization with the target sequence. A probe may be bound to an additional nucleic acid sequence, such as a poly-T tail used to immobilize the probe, without significantly altering the hybridization characteristics of the probe. One of skill in the art will recognize that for use in the present methods, a probe bound to an additional nucleic acid sequence which is not complementary to the target sequence and, thus, is not involved in the hybridization, is essentially equivalent to the unbound probe.

Preferably, a nucleic acid sequence from the *N. gonorrhoeae* Ng-CDMT sequence gene which contains one or more variable positions is amplified prior to hybridization with oligonucleotide probes under suitably stringent hybridization conditions. The amplification is carried out to provide sufficient nucleic acid for analysis by probe hybridization. In this embodiment, the simultaneous amplification of related non-target sequences is not a problem in this embodiment because sequence specificity is provided by a probe hybridization step. Thus, any primers which amplify a region of the *N. gonorrhoeae* Ng-CDMT gene encompassing the variable positions are suitable.

Methods for Detecting Nucleic Acid

The methods of the present invention involve either amplification of a region of the Ng-CDMT gene followed by detection using an *N. gonorrhoeae*-specific probe of the present invention, or amplification of a region of the Ng-CDMT gene using an *N. gonorrhoeae*-specific primer of the present invention followed by detection of the amplified nucleic acid, preferably using a probe. Methods for detecting target nucleic acid by hybridization with complementary oligonucleotide probes are well known in the art. The particular assay format is not a critical aspect of the invention. Suitable assay formats for detecting target-probe hybridization include the dot-blot and reverse dot-blot assay formats.

In a dot-blot format, the amplified target DNA is immobilized on a solid support, such as a nylon membrane. The membrane-target complex is incubated with labeled probe under suitable hybridization conditions, unhybridized probe is removed by washing under suitably stringent conditions, and the membrane is monitored for the presence of bound probe. Dot-blot detection of PCR amplification products is described in, for example, Saiki et al, 1986, *Nature* 324:163–166 and U.S. Pat. No. 5,468,613, both incorporated herein by reference.

In the reverse dot-blot format, the probes are immobilized on a solid support, such as a nylon membrane and the amplified target DNA is labeled. The target DNA is typically labeled during amplification by the incorporation of labeled primers. One or both of the primers can be labeled. The membrane-probe complex is incubated with the labeled amplified target DNA under suitable hybridization conditions, unhybridized target DNA is removed by washing under suitably stringent conditions, and the filter is then monitored for the presence of bound target DNA. Reverse dot-blot methods are described in, for example, Saiki et al, 1989, *Proc. Natl. Acad. Sci. USA* 86:6230 and U.S. Pat. No. 5,468,613, both incorporated herein by reference.

Alternatively, the reverse dot-blot assay can be carried out using a solid support having a plurality of probe hybridization sites or wells. For example, a microwell plate is particularly useful in large scale clinical applications of the present methods. Probes can be immobilized to a microwell plate either by passive binding or through a protein intermediate, such as bovine serum albumin (BSA), which adheres to microwell plates (see Tung et al., 1991, *Bioconjugate Chem.* 2:464–465, incorporated herein by reference). Reverse dot-blot methods for the detection of an amplified *N. gonorrhoeae* sequence carried out in a microwell plate are described in U.S. Pat. No. 5,550,040 and the product insert of the AMPLICOR® *Chlamydia trachomatis/Neisseria gonorrhoeae* (CT/NG) Test. The use of a microwell plate assay is described further in the examples.

Alternatively, BSA-conjugated probes are bound to magnetic microparticles. The bound probes are hybridized in solution to labeled amplification product, and the resulting hybridization duplexes are removed from the solution magnetically. The magnetically immobilized hybridization duplexes are then detected as in the methods described above.

Another suitable assay method, referred to as a 5'-nuclease assay, is described in U.S. Pat. Nos. 5,210,015, and 5,487,972 and Holland et al., 1988, *Proc. Natl. Acad. Sci. USA* 88:7276–7280, each incorporated herein by reference. In the 5'-nuclease assay, labeled detection probes which have been modified so as to prevent the probes from acting as primers for DNA synthesis are added during the amplification reaction mixture. Any probe which hybridizes to target DNA during each synthesis step, i.e., during primer extension, is degraded by the 5' to 3' exonuclease activity of the DNA polymerase, e.g., Taq DNA polymerase. The degradation product from the probe is then detected. Thus, the presence of probe breakdown product indicates both that hybridization between probe and target DNA occurred and that the amplification reaction occurred. U.S. Pat. Nos. 5,491,063 and 5,571,673, both incorporated herein by reference, describe improved methods for detecting the degradation of probe which occurs concomitant with amplification.

The assay formats described above typically utilize labeled oligonucleotides to facilitate detection of the hybrid duplexes. Oligonucleotides can be labeled by incorporating a label detectable by spectroscopic, photochemical, biochemical, immunochemical, or chemical means. Useful labels include $^{32}$P, fluorescent dyes, electron-dense reagents, enzymes (as commonly used in ELISA's), biotin, or haptens and proteins for which antisera or monoclonal antibodies are available. Labeled oligonucleotides of the invention can be synthesized and labeled using the techniques described above for synthesizing oligonucleotides.

An alternative method for detecting the amplification of *N. gonorrhoeae* nucleic acid by monitoring the increase in the total amount of double-stranded DNA in the reaction mixture is described in Higuchi et al., 1992, *Bio/Technology* 10:413–417; Higuchi et al., 1993, *Bio/Technology* 11:1026–1030; and European Patent Publication No. 512, 334, each incorporated herein by reference. The detection of double-stranded target DNA relies on the increased fluorescence that ethidium bromide (EtBr) and other DNA binding dyes exhibit when bound to double-stranded DNA. The DNA binding label is added to the amplification reaction mixture. Amplification of the target sequence results in an increase in the amount of double-stranded DNA, which results in a detectable increase in fluorescence.

The present invention also relates to kits, multicontainer units comprising useful components for practicing the present method. A useful kit contains oligonucleotides of the present invention, such as, depending on the intended use, *N. gonorrhoeae*-specific primers or *N. gonorrhoeae*-specific probes. Other optional components of the kit include, for example, amplification reaction reagents, such as an agent to catalyze the synthesis of primer extension products, the substrate nucleoside triphosphates, means used to label (for example, an avidin-enzyme conjugate and enzyme substrate and chromogen if the label is biotin), the appropriate buffers for PCR or hybridization reactions, and instructions for carrying out the present method.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLE 1

Reaction Protocols

This examples describes reaction protocols for the amplification and detection of *N. gonorrhoeae* DNA which were used in the following examples.

Sample Preparation

Throat swab specimens were collected using the AMPLICOR (STD Swab Sample Collection and Transport Kit (Roche Diagnostics Systems, Branchburg, N.J.), as follows. Throat swab specimens were placed into sample transport medium (STM) consisting of 0.4% sodium dodecyl sulfate and 10 mM Tris-HCl, pH 8.0. The swabs were vigorously agitated in the STM for 15 seconds, the liquid was expressed against the side of the tube, and the swabs were removed.

Prior to amplification, the sample was heated to 95(C. for 10 minutes to lyse the cells, cooled to room temperature, and mixed with an equal volume of specimen diluent (SD) consisting of 20% Tween-20 (polyoxyethlene-sorbitan monolaurate), 10 mM Tris-HCl, pH 8.0, and 0.10% sodium azide. The sample was then vortexed for 5–10 seconds and incubated at room temperature for at least 10 minutes (but no longer than 2 hours).

Samples of cells were prepared as described for throat swab specimens.

Purified DNA samples were diluted in an equal volume of STM and SD and incubated at room temperature without heating.

Amplification

Each amplification was carried out using two pairs of primers to enable the simultaneous amplification of nucleic acid from *Chlamydia trachomatis* and *N. gonorrhoeae*. Primers CP24 and CP27, specific for the amplification of *C. trachomatis*DNA, were included in all reactions. For the amplification of *N. gonorrhoeae*, a primer pair consisting of an upstream primer selected from SS01, JW79 (SEQ ID NO: 2), or JW80 (SEQ ID NO: 3) together with downstream primer SS02 was used. Primers CP24, CP27, SS01, and SS02 are described fully in U.S. Pat. No. 5,550,040, incorporated herein by reference.

PCR amplifications were carried out in a total reaction volume of 100 (1 consisting of 50 (1 of DNA sample or clinical specimen added to 50 (1 of reaction mixture. The final reaction concentrations were as follows:

25 pmol each primer
50 (M each dATP, dCTP, and dGTP
150 (M dUTP
50 mM KCl
10 mM Tris-HCl, pH 8.3

1.5 mM $MgCl_2$
10% glycerol
5 U Taq DNA polymerase*
2 U uracil-N-glycosylase*

* developed and manufactured by Roche Molecular Systems and marketed by Perkin Elmer (Norwalk, Conn.).

Reactions were carried out in a GeneAmp PCR System 9600 (Perkin Elmer, Norwalk, Conn.) using the following thermal cycling conditions:

| Step | | Time |
|---|---|---|
| Incubate | | 2 minutes, 50(C |
| | | 5 minutes, 95(C |
| 35 cycles | denature | 20 seconds, 95(C |
| | anneal | 20 seconds, 62(C |
| | extend | 20 seconds, 72(C |
| hold | | >10 minutes, 72(C |

Detection

Amplified product was detected in microwell plate assays using the *C. trachomatis*-specific probe, CP35, and the *N. gonorrhoeae*-specific probe, SS06-T5, using the high-stringency hybridization buffer (4.0 M NaSCN), as described in U.S. Pat. No. 5,550,040, incorporated herein by reference. Signals (measured at 450 nm) less than or equal to 0.25 were judged to be negative, signals between 0.25 and 1.0 were judged to be ambiguous, and signals greater than 1.0 were judged to be positive.

EXAMPLE 2

Specificity Within Neisseria Genus

To assess the specificity of the primer pairs, amplifications were carried out using purified target DNA or dilutions of cells from various strains of Neisseria species. The samples were amplified in duplicate reactions and assayed in microwell plate hybridization assays using the protocols described above. Samples of cells and purified DNA samples contained at least $10^6$ copies of target DNA, with the exception that a sample of *N. gonorrhoeae* was also used at a concentration of 100 copies per reaction.

The following primer pairs were compared:

| Upstream Primer | Downstream Primer |
|---|---|
| SS01 | SS02 (SEQ ID NO: 5) |
| JW79 (SEQ ID NO: 2) | SS02 (SEQ ID NO: 5) |
| JW80 (SEQ ID NO: 3) | SS02 (SEQ ID NO: 5) |

Amplified samples were assayed by hybridization with the *N. gonorrhoeae*-specific probe in a microwell plate assay as described in Example 1. The results of the hybridizations are presented in the table below. Positive, ambiguous, and negative signals are denoted as "+", "±", and "−", respectively.

The nomenclature of *N. subflava* has not been resolved fully. One classification, still used in some current literature, considers as separate species *N. subflava*, *N. perflava*, and *N. flava*. Since 1974, the species *N. subflava, N. perflava*, and *N. flava* have been reclassified as variants of a single species, *N. subflava*. These variants of *N. subflava* are characterized as three biovars of *N. subflava* (biovar subflava, biovarflava, and biovar perflava) that can be distinguished biochemically and microbiologically. The nomenclature of *N. subflava* used in the table follows this convention. Those isolates for which the biovar was not determined are designated *N. subflava*.

| Species | SS01/SS02 | JW79/SS02 | JW80/SS02 |
|---|---|---|---|
| *N. gonorrhoeae**  | + | + | + |
| *N. gonorrhoeae* | + | + | + |
| *N. cinerea* | − | − | − |
| *N. cinerea* | − | − | − |
| *N. cinerea* | + | − | − |
| *N. cinerea* | − | − | − |
| *N. cinerea* | + | − | − |
| *N.g. kochii* | − | − | − |
| *N. mucosa* | − | − | − |
| *N. mucosa* | − | − | − |
| *N. mucosa* | − | − | − |
| *N. mucosa* | − | − | − |
| *N. mucosa* | − | − | − |
| *N. subflava* | − | − | − |
| *N. subflava* | + | − | − |
| *N.s. subflava* | − | − | − |
| *N. subflava* | − | − | − |
| *N.s. flava* | + | +/− | − |
| *N.s. subflava/flava* | − | − | − |
| *N.s. perflava* | − | − | − |
| *N.s. perflava* | − | − | − |
| *N.s. perflava* | − | − | − |
| *N.s. perflava* | − | − | − |
| *N.s. perflava* | + | − | − |
| *N.s. perflava* | + | − | − |
| *N.s. perflava* | + | − | − |
| *N.s. perflava* | − | − | − |
| *N.s. perflava* | − | − | − |
| no DNA | − | − | − |
| no DNA | − | − | − |

*100 copies of purified DNA

*N. gonorrhoeae* was detected using all three pairs of primers. The successful amplification of 100 copies of target indicate that the primers of the present invention provide equivalent sensitivity.

Using primers SS01 and SS02 (SEQ ID NO: 5), false positive results were observed from 2/5 of the strains of *N. cinerea* and 5/15 of the strains of *N. subflava*. Use of JW79 (SEQ ID NO: 2) as the upstream primer eliminated all false positive results, although an ambiguous result was observed from one isolate of *N. subflava*. Use of JW80 (SEQ ID NO: 3) as the upstream primer eliminated all false positive results.

EXAMPLE 3

Specificity with Throat Swab Specimens

Throat swab specimens obtained from normal volunteers were prepared as described in Example 1. All specimens were free of infection with *N. gonorrhoeae*, as determined by an independent assay. Amplifications were carried out using the primer combinations described in Example 2. Amplified samples were assayed by both gel electrophoresis and by hybridization with the *N. gonorrhoeae*- and *C. trachomatis*-specific probes in microwell plate assays as described in Example 1.

All specimens were negative for *C. trachomatis* DNA. The results obtained from the hybridizations with the *N. gonorrhoeae*-specific probe are presented in the table below. Positive, ambiguous, and negative signals are denoted as "+", "±", and "−", respectively.

| Throat Swab (50 μl) | SS01/SS02 | JW79/SS02 | JW80/SS02 |
|---|---|---|---|
| 1 | + | − | − |
| 2 | − | − | − |
| 3 | − | − | − |
| 4 | + | − | − |
| 5 | + | − | − |
| 6 | − | − | − |
| 7 | + | − | − |
| 8 | − | − | − |
| 9 | + | − | − |
| 10 | + | − | − |
| 11 | − | − | − |
| 12 | + | − | +/− |
| 13 | + | − | − |
| 14 | − | − | − |
| 15 | − | − | − |
| 16 | + | − | − |
| 17 | − | − | − |
| 18 | − | − | − |
| 19 | + | − | − |
| 20 | − | − | − |
| 21 | − | − | − |
| 22 | − | − | − |
| 23 | − | − | − |
| no DNA | − | − | − |

Using primers SS01 and SS02 (SEQ ID NO: 5), false positive results were observed from 10/23 of the clinical throat swab samples. Use of JW79 (SEQ ID NO: 2) as the upstream primer eliminated all false positive results. Use of JW80 (SEQ ID NO: 3) as the upstream primer eliminated all false positive results, although an ambiguous result was observed from one sample.

I claim:

1. A *Neisseria gonorrhoeae*-specific oligonucleotide, wherein said oligonucleotide consists of a nucleotide sequence between about 15 and about 50 nucleotides in length substantially complementary to a *Neisseria gonorrhoeae* cytosine DNA methyltransferase gene that is SEQ ID NO: 1 in a region which encompasses a nucleotide position selected from nucleotide positions numbers 618, 621, 627, 630, 636, 653, 654, 669, 678, 681, 683, and 702; wherein said sequence is exactly complementary to SEQ ID NO: 1 at each nucleotide position selected from nucleotide positions numbers 618, 621, 627, 630, 636, 653, 654, 669, 678, 681, 683, and 702 encompassed within said region, and wherein said *Neisseria gonorrhoeae*-specific oligonucleotide is capable of distinguishing by selective hybridization said *Neisseria gonorrhoeae* cytosine DNA methyltransferase gene from cytosine DNA methyltransferase genes from Neisseria strains that differ in nucleotide sequence from SEQ ID NO: 1 at nucleotide position numbers 618, 621, 627, 630, 636, 653, 654, 669, 678, 681, 683, and 702.

2. An oligonucleotide of claim 1, wherein said oligonucleotide consists of a nucleotide sequence exactly complementary to either strand of SEQ ID NO: 1 in a region which encompasses a nucleotide position selected from nucleotide positions numbers 618, 621, 627, 630, 636, 653, 654, 669, 678, 681, 683, and 702.

3. An oligonucleotide of claim 1, wherein said region encompasses two nucleotide positions selected from nucleotide positions numbers 618, 621, 627, 630, 636, 653, 654, 669, 678, 681, 683, and 702.

4. An oligonucleotide of claim 1, wherein said region has a 5′ terminal position selected from nucleotide positions numbers 618, 621, 627, 630, 636, 653, 654, 669, 678, 681, 683, and 702.

5. An oligonucleotide of claim 1 that is JW79 (SEQ ID NO: 2), JW80 (SEQ ID NO: 3), or JW87 (SEQ ID NO: 4).

6. A pair of oligonucleotide primers consisting of an oligonucleotide of claim 5 and an oligonucleotide that is SS02 (SEQ ID NO: 5), JW88 (SEQ ID NO: 6), JW89 (SEQ ID NO: 7), or JW90 (SEQ ID NO: 8).

7. A kit for detecting *Neisseria gonorrhoeae* nucleic acid, wherein said kit comprises an oligonucleotide of claim 1.

8. A kit for detecting *Neisseria gonorrhoeae* nucleic acid, wherein said kit comprises an oligonucleotide of claim 2.

9. A kit for detecting *Neisseria gonorrhoeae* nucleic acid, wherein said kit comprises an oligonucleotide of claim 3.

10. A kit for detecting *Neisseria gonorrhoeae* nucleic acid, wherein said kit comprises an oligonucleotide of claim 4.

11. A kit for detecting *Neisseria gonorrhoeae* nucleic acid, wherein said kit comprises an oligonucleotide of claim 5.

12. A kit for amplifying *Neisseria gonorrhoeae* nucleic acid, wherein said kit comprises a pair of oligonucleotide primers of claim 6.

13. A method for detecting *Neisseria gonorrhoeae* nucleic acid, wherein said method comprises:

(a) carrying out a polymerase chain reaction using a pair of primers, wherein said pair of primers comprises a *Neisseria gonorrhoeae*-specific primer that consists of a nucleotide sequence between about 15 and about 50 nucleotides in length substantially complementary to a *Neisseria gonorrhoeae* cytosine DNA methyltransferase gene that is SEQ ID NO: 1 in a region which encompasses a nucleotide position selected from nucleotide positions numbers 618, 621, 627, 630, 636, 653, 654, 669, 678, 681, 683, and 702; wherein said sequence is exactly complementary to SEQ ID NO: 1 at each nucleotide position selected from nucleotide positions numbers 618, 621, 627, 630, 636, 653, 654, 669, 678, 681, 683, and 702 encompassed within said region; wherein said *Neisseria gonorrhoeae*-specific primer is capable of distinguishing by selective hybridization said *Neisseria gonorrhoeae* cytosine DNA methyltransferase gene from cytosine DNA methyltransferase genes from Neisseria strains that differ in nucleotide sequence from SEQ ID NO: 1 at nucleotide position numbers 618, 621, 627, 630, 636, 653, 654, 669, 678, 681, 683, and 702; and wherein said polymerase chain reaction is carried out under conditions such that amplification occurs only if said *Neisseria gonorrhoeae* nucleic acid is present in said reaction; and (b) detecting amplified *Neisseria gonorrhoeae* nucleic acid.

14. A method of claim 13, wherein said *Neisseria gonorrhoeae*-specific primer consists of a nucleotide sequence exactly complementary to either strand of SEQ ID NO: 1 in a region which encompasses a nucleotide position selected from nucleotide positions numbers 618, 621, 627, 630, 636, 653, 654, 669, 678, 681, 683, and 702.

15. A method of claim 13, wherein said region encompasses two nucleotide positions selected from nucleotide positions numbers 618, 621, 627, 630, 636, 653, 654, 669, 678, 681, 683, and 702.

16. A method of claim 13, wherein said region has a 5' terminal position selected from nucleotide positions numbers 618, 621, 627, 630, 636, 653, 654, 669, 678, 681, 683, and 702.

17. A method claim 13, wherein said *Neisseria gonorrhoeae*-specific primer is JW79 (SEQ ID NO: 2), JW80 (SEQ ID NO: 3), or JW87 (SEQ ID NO: 4).

18. A method of claim 13, wherein said pair of primers consists of a *Neisseria gonorrhoeae*-specific primer that is JW79 (SEQ ID NO: 2), JW80 (SEQ ID NO: 3), or JW87 (SEQ ID NO: 4); and a primer that is SS02 (SEQ ID NO: 5), JW88 (SEQ ID NO: 6), JW89 (SEQ ID NO: 7), or JW90 (SEQ ID NO: 8).

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 1067 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:1:

```
ATGCTATCTA AACAAATCTC AAATCTTAAT TCTTCTAGTA ACAAACCAAA AATCCTATCT      60

CTATTTTCAG GATGTGGCGG TTTGTATTTG GGCTTTCATC AAGCTGGTTG TGAAACTGTT     120

TGGGCGAACG ATTTCTCCCA TTGGGCTTGC GAAAGTTTCC GTAAAAATAT CGGCGATGTC     180

ATCGTAGAAG GTGATATTGA ACAAATTAAT CCGAATGATC CAACTATTCC CGATTGCGAC     240

ATCATTTTAG GCGGATTCCC TTGTCAAGAT TTTTCCATGA TTTGGAAACA GCCGGGCTTA     300

GAGGGTGAGC GCGGCAATCT TTATAAAAGC TTTTTACGTT TTGTAAATGC AAAAAAACCG     360

AAAGTTTTTG TTGCTGAGAA TGTGAAAGGT TTATTGACTG CCAACAAGAA AAAAGCCATC     420

CAGCAAATTA TTACCGACTT TGAAAATTGC GGTTATTACG TTCAGGCGAA GCTGTATAAC     480

TTTGCAGAAT TTGGCGTACC TCAATTTCGT GAACGTGTGC TGATTGTCGG AGTACGTTTG     540

GATACAGGAT TTGATTTTCG CCATCCGGAA CCGACGCACA ATGAAACTGG CGAAAACGGC     600

TTAAAACCAT ATGTAACAGC AGGTCAGGCC ATATCCAATA TTCCACAAAA TGCCAGTAAT     660

AATGAATTAC TGAAAATCAG CGGTAAAACA CGCCGTATGT TCGAATTAAT TCCTGAAGGT     720

GGAAATTTTA CCGATATTCC TAAAGATCAT CCTTTATATG TGAAAGGTAT GATTAGCCAC     780

GTTTATCGTC GTATGCATCG GAACGAGCCA TCAAAAACAA TTATTGCAGC AGGTGGCGGT     840

GGTACTTGGG GCTATCACTT CCCTGAACCG CGTGCTTTTA CTAATAGAGA ACGAGCAAGG     900

CTTCAAAGTT TTCCTGATGA TTTTGAGTTT GTCGGATCAA CAACTGAAGT ACGTCGCCAG     960
```

```
ATTGGTAATG CTGTTCCTCC TCAGGGCGTG GTTGAACTGG CAAAAAGCAT TTTACCGATT    1020

TTTTCAGACA ACTATGAGAA AGTAGATTTG CATGAGAAAT TAGTCGA                  1067
```

(2) INFORMATION FOR SEQ ID NO:2:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
CATATGTAAC AGCAGGTCAG GCC                                              23
```

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
TAACAGCAGG TCAGGCCATA TCC                                              23
```

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
CGGTAAAACA CGCCGTATGT TC                                               22
```

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
AACAGCATTA CCAATCTGGC GAC                                              23
```

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
GACGTACTTC AGTTGTTGAT CCG                                              23
```

-continued (2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CGACGTACTT CAGTTGTTGA TCCG        24

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CAGTTGTTGA TCCGACAAAC TCA        23